United States Patent [19]

Breneman

[11] Patent Number: 4,818,707

[45] Date of Patent: Apr. 4, 1989

[54] DEVICE AND MIXTURE FOR TESTING FOR IMMUNE RESPONSES TO FOOD

[76] Inventor: James C. Breneman, 10571 Miller Dr., Galesburg, Mich. 49053

[21] Appl. No.: 721,405

[22] Filed: Apr. 9, 1985

Related U.S. Application Data

[62] Division of Ser. No. 487,065, Apr. 21, 1983, Pat. No. 4,543,964.

[51] Int. Cl.$^4$ .......................................... G01N 33/053
[52] U.S. Cl. ..................................... 436/513; 424/88; 422/56; 422/58; 128/743; 436/807; 436/810
[58] Field of Search ..................... 436/513, 807, 810; 128/743; 422/56, 58; 424/88

[56] References Cited

U.S. PATENT DOCUMENTS

| | | | |
|---|---|---|---|
| 2,278,339 | 3/1942 | Vollmer | 128/743 |
| 3,212,495 | 10/1965 | Osbourn | 128/743 |
| 3,894,531 | 7/1975 | Saunders | 128/743 |
| 4,312,865 | 1/1982 | Szucs | 514/174 X |
| 4,450,844 | 5/1984 | Quisno | 128/743 |
| 4,711,247 | 12/1987 | Fishman | 128/743 |

OTHER PUBLICATIONS

Chemical Abstracts, 90:29050k, (1979).

*Primary Examiner*—Sidney Marantz
*Attorney, Agent, or Firm*—Price, Heneveld, Cooper, DeWitt & Litton

[57] ABSTRACT

A device for the detecting of an individual's Gell-Coombs Types I, II, III and IV immune response reactions to edible substances includes a mixture of an edible substance and a solution of non-toxic aprotic solvent, such as DMSO and water. The solvent acts as a carrier transporting the food beneath the skin. The device holds the mixture against the skin and prevents evaporation of the solution. The method includes the preparation of a plurality of mixtures of different edible substances and a solution of non-toxic aprotic solution, the application of the mixture to the skin of the individual and the holding of the mixture on the skin for a predetermined period of time. The mixture is subsequently removed, and the site is inspected to determine whether a Type I, II, III or IV Gell-Coombs immune response reaction has occurred. Control sites containing the solvent only and a control site containing a food substance which causes the skin to fluoresce upon exposure to an ultraviolet light may also be used. Fluorescence indicates whether the mixtures have been in sufficient contact with the skin for the required period of time.

15 Claims, 1 Drawing Sheet

FIG. 2 (ENLARGED)

DEVICE AND MIXTURE FOR TESTING FOR IMMUNE RESPONSES TO FOOD

This is a divisional of Application Ser. No. 487,065, filed Apr. 21, 1983, and now U.S. Pat. No. 4,543,964.

BACKGROUND OF THE INVENTION

The present invention relates to the testing of an individual for immune reactions to ingestants, including foods, and in particular, to a unique, simple and relatively inexpensive device and method for determining food hypersensitivity and for identifying different types of immune reactions against specific foods and chemicals.

There are four generally recognized types of immune responses to foods which are commonly referred to as Gell-Coombs Types I, II, III and IV. Type I is characterized by the involvement of immunoglobulin "E" (IgE) antibodies which are produced by specific B-lymphocytes in response to the particular food. It was known that sensitized IgE antibodies were resident under the skin, as well as many other tissues and organs. Foods producing a Type I immune response could be tested through the skin by injecting into cutaneous layers of skin an aqueous solution of the food producing the Type I response. Prick tests could also be employed with aqueous food solutions. Therefore, food producing a Type I reaction could be tested intradermally. The immune response could be detected for a given food if redness or swelling appeared at the injection or prick test site. Type I responses may also be tested by Raido allergo sorbent testing (RAST).

Gell-Coombs Types II and III are characterized by the involvement of immunoglobulin "G" (IgG), immunoglobulin "M" (IgM), and some special IgE antibodies. Heretofore, intradermal tests were unable to produce a reliable immune response in the skin to foods producing a Type II or Type III immune response. This was largely true for the fat-soluble foods producing a Type II or Type III response. Fat-soluble foods being insoluble in water and, of course, not adaptable to the introduction through or into the skin in aqueous solution by means of a prick test or injection. This was also true for water-soluble foods producing a Type II or Type III immune response.

Consequently, when an individual was suspected clinically to have a Type II or Type III reaction to a particular food, an elimination diet was typically prescribed to detect the suspect food. An elimination diet involves initially restricting a patient's intake to foods which usually are hyporeactive. Pure foods are then introduced one-by-one as challenges into the diet to assess whether the person is hypersensitive to the added foods. The elimination diet can also be used for the detection of Type I immune responses.

The problems with the elimination diet are multiple. First, the elimination diet depends upon the patient experiencing discomfort or obvious organ dysfunction, usually a subjective evaluation. Any immune responses not producing discomfort or obvious organ dysfunction would not be detected by the elimination diet technique. Second, the elimination diet will detect discomforts or organ dysfunctions which are not related to immune responses to foods. For instance, the individual may have duodenal ulcers, colitis, gout, or gall bladder problems which produce discomfort when certain foods are eaten. These discomforts and dysfunctions are, however, not related to the individuals immune responses to the particular food. Therefore, the elimination diet may have misleading results. Thirdly, the elimination diet is very time consuming. An individual having to be on the elimination diet for several months is not at all unusual.

Finally, human weaknesses undermine accurate determination of an individual's immune response to given foods. It is difficult for some patients to eliminate from their diets certain foods to which they may be sensitive. Such foods are widespread in our food supply; they include chicken, beef, pork, chocolate, eggs, milk, coffee, peanuts, tomatoes and wheat, to name a few. Immune responses to foods not on the patient's diet can mask immune responses to foods under study or mislead the practitioner into believing that a food under study produces an immune response when in fact the food produces no such response.

If the elimination diet fails to lead to the detection of an immune response to a given food, there are a number of alternative tests which can be employed. For Type II immune responses, the hemaglutinations test, the complement depletion test, or a tissue biopsy can be performed. All of these tests are indirect, time-consuming, expensive and often inaccurate. These same tests can also be used to detect a Type III reaction. In addition, the Raji-Cell Test or a nephelometry test can be used to detect a Type III reaction. These tests are also time-consuming, expensive and often inaccurate because of technical intracacies.

The Type IV Gell-Coombs reaction involves sensitized lymphocytes or T-cells which respond to a specific food and which are believed to be at least as specific as an antibody to the food producing the immune response. Two tests have heretofore been available, namely, the migration inhibition factor test and the lymphoblastogenesis test. These tests are extremely expensive, each food presently costing approximately $2,000 to test. The tests are time-consuming as well, taking approximately 3-4 weeks.

As should be apparent, the diagnosis and treatment of immune reactions to ingestants has involved relatively expensive and complicated diagnostic tests. The laboratory tests are sophisticated and impractical for use in the average office facility. There has been a longfelt and unfulfilled need for a relatively simple, accurate, and inexpensive test which may be readily used by the practitioner.

SUMMARY OF THE INVENTION

In accordance with the present invention the aforementioned needs are fulfilled by providing an inexpensive, simple and quick test for detecting an individual's Type I, II, III and IV Gell-Coombs immune responses to various foods. Essentially, the test involves the application to the skin of a mixture of an ingestible substance (either food, chemical or drug) to be tested and a solution of a non-toxic aprotic solvent and water. One known solvent is dimethyl sulphoxide (DMSO). The mixture is held against the skin to prevent the solvent from evaporating or absorbing excessive amounts of atmosphere water. The mixture is applied to the skin in a sufficient amount and concentration such that an immune response reaction can be detected if the individual is sensitive to the edible substance tested.

A solvent such as DMSO has the ability to penetrate the skin and act as a carrier. DMSO is a solvent of both fat and water soluble food products and will carry the antigen from the food through the skin. The lower layers of the skin have been found to have certain sensitized immune structures which will produce Gell-Coombs Types I, II, III and IV immune responses.

A prime advantage resulting from the present invention is that immune responses to a plurality of foods can be tested in just several days. The procedure is much less expensive than any other known techniques. Furthermore, the results correlate well with standard test results and clinical responses.

In one embodiment of the present invention, a DMSO-food mixture is applied to the skin by means of a cotton-gauze patch held in place by an adhesive strip. In another embodiment, the mixture is applied to the skin by means of a test patch with a plurality of cells, each of which contains a quantity of DMSO solution or an equivalent solvent and a quantity of a dried food. In still another embodiment, the mixture is contacted with the skin by means of a stainless steel cap in which cotton and the mixture is placed. The stainless steel or aluminum cap is held on the skin by means of an adhesive strip. In each of the above embodiments, methyl-cellulose can be used in place of cotton.

In a further embodiment, a test strip with a plurality of cells is applied to the skin, each cell containing a food-solvent mixture, wherein at least one cell contains a food which, after several days of exposure to the skin, will cause the skin to fluoresce under an ultraviolet light providing an indicator of whether or not the test patch has remained on the skin securely for the required period of time.

DETAILED DESCRIPTION OF THE PREFERRED EMBODIMENTS

Figure 1:
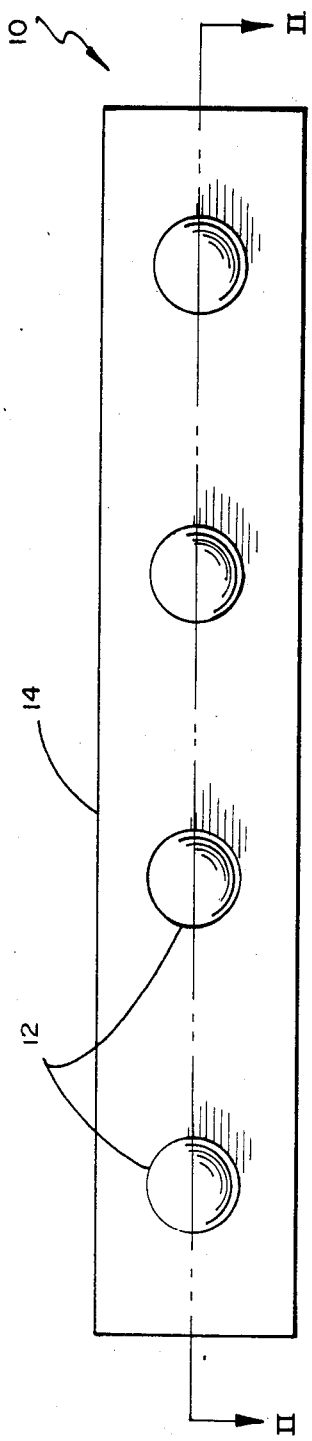
FIG. 1 is a top, plan view of a test patch in accordance with the present invention.
Figure 2:
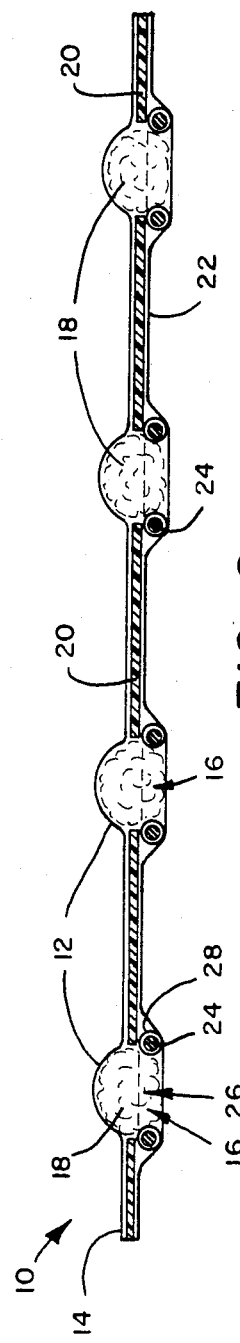
FIG. 2 is a cross-sectional view, taken generally along line II—II of FIG. 1.

A test strip in accordance with the present invention is shown in FIGS. 1 and 2 and designated 10. Test strip 10 includes a plurality of cells 12 on a sheet 14. Each cell extends through a hole 16 in sheet 14, as shown in FIG. 2. Holes 16 are not essential. The sheet can extend over cells 12. An absorbent material 18, such as cotton or methyl cellulose is placed in each cell 12. The absorbent material is impregnated with an amount of the solution-dried food mixture. An adhesive 20 is applied to the underside of sheet 14 on the areas between cells 12. A backing sheet 22 is employed to retain the mixtures within the cells during storage. It should be understood that the strip 10 may include more than the four cells illustrated in FIG. 1.

When patch test kit 10 is applied to the skin, the DMSO can dissolve the adhesive and carry adhesive products through the skin. As a result, an annular or O-ring 24 made from a resilient material is placed around the periphery of openings 16 of each cell 12. The resilient rings are, in turn, wrapped in a DMSO-insoluble material 28 to prevent the DMSO from dissolving the rings and carrying the dissolved material through the skin. Metal foils, especially aluminum foils, have been found to be particularly useful wrapping materials. Cells 12 can be made from a foil such as aluminum foil. The foil defining the cell also serves as the wrapping material to prevent the DMSO from dissolving resilient rings 24. However, cells 12 can be made from any material substantially insoluble in DMSO. Non-toxic, hypoallergenic soluble materials could also be used.

Figure 3:
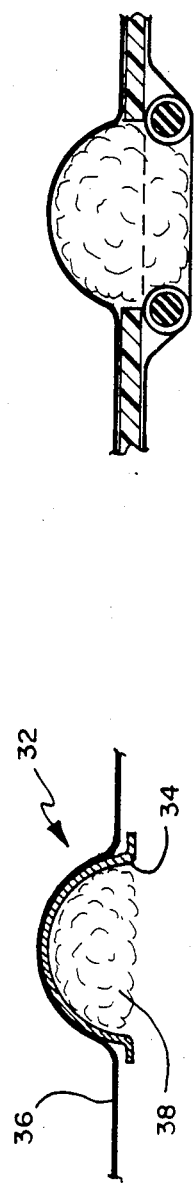
FIG. 3 is a cross-sectional view of an alternate embodiment of the present invention.

Another structure for applying the solvent-food mixtures is shown in FIG. 3 and designated by the numeral 32. Device 32 includes a semi-spherical stainless steel cap 34 and an adhesive coated strip 36. A quantity of absorbent material such as methyl cellulose or cotton 38 is placed inside cap 34 before application to the skin. Absorbent material 38 contains a small amount of the food-solvent mixture. The absorbent material helps to keep the mixture within the cap.

Any absorbent material used in the manner described herein should be of a type which will not dissolve in the solution and be transported through the skin. It has been found that cotton or methyl cellulose do not dissolve in DMSO. Furthermore, neither of these materials typically cause an immune response when contacted with the skin which could be confused with an immune response due to food antigens.

It is believed that any non-toxic aprotic solvent can be used consistent with the teachings of the present invention. However, DMSO is the preferred solvent because of its demonstrated ability to penetrate the skin and its ability to dissolve both fat soluble and water soluble material which is characteristic of aprotic solvents.

The DMSO solution need not be pure DMSO. A ninety percent (90%) by volume DMSO solution works well for this application. It is believed that a DMSO solution of only about twenty percent (20%) by volume, the balance being essentially water, would work as well. The food-DMSO solution mixture may consist of five milliliters of DMSO solution for every gram of dried food. The DMSO-dried food mixtures can be mixed in large batches in the same 5:1 ratio if mass production is desired. The 5:1 ratio is not believed to be critical, however. Other ratios will probably be as effective in producing the desired immune responses to the tested foods. The mixtures must be stored in glass or metal containers, as contrasted with plastic or other synthetic material which may be partially dissolved by the DMSO.

Usually, only about a drop or about 0.05 milliliters of the 5:1 DMSO-food mixture need be applied to the skin in order to produce a localized, detectable reaction. Thus, if the test strip shown in FIG. 1 is used, a drop of a food-DMSO mixture should be applied in each of cells 12 in absorbent material 16. A similar quantity would be used in the device shown in FIG. 3. A drop of 5:1 DMSO-food mixture is sufficient to produce a localized immune response on the skin of either Gell-Coombs Types I, II, III or IV.

Alternatively, the mixture could be prepared as a gell to simplify storage and application. Methyl cellulose would be mixed with water until in gell form. The food antigen and DMSO solution in the ratio of 1 gram of food to 5 milliliters of DMSO would then be thoroughly mixed into the gell. The resulting preparation may be stored in a tube and dispensed for testing merely by squeezing the tube. The gell preparation may be dispensed into the cells of the patch test strip 10 or the cup of device 32.

Before applying the solvent-food mixture to the skin, the practitioner should thoroughly clean the surface of the skin on which the mixture is to be applied. Only water should be used, however. If the skin is not thoroughly cleaned with water before the mixture is applied, perfumes, soaps, and the like on the skin may be carried through the skin by the DMSO and may produce a confusing immune reaction. It should be apparent that no soap should be used in cleaning the skin, as it will be carried through the skin as well.

Once the DMSO-food mixture is applied to the skin in any one of the above methods, the evaporation prevention means (e.g. the adhesive bandage, the patch test or the stainless steel cap) is removed after about thirty (30) minutes. Any Type I immune response reactions can be observed on the skin at such time. Types II, III and IV are delayed reactions, so the evaporation prevention means should be replaced after checking for Type I reactions.

Types II, III and IV reactions can be observed on the skin after a mixture has been in contact with the skin for about three (3) days. Therefore, after three (3) days, the evaporation prevention means is removed and the Types II, III and IV reactions can be observed.

Typically, Types I, II, III and IV immune responses on the skin have been found to manifest themselves in erythema, edema, vessicles or bullae. Slight immune response reactions are typically characterized by minimal erythema. Moderate response reactions are typically evidenced by erythema and edema, perhaps in conjunction with early vessicle formation. An intense immune response reaction will be characterized by significant erythema, significant edema, vessicles, and bullae. Five grades can be assigned to skin immune response reactions, accordingly:

Tr—Minimal erythema
1—Significant erythema
2—Significant erythema and edema (palpable elevation)
3—Significant erythema, significant edema and early vessicle
4—Significant erythema, significant edema, vessicle and bullae.

Based upon initial studies, the DMSO itself can produce erythema, particularly if a more concentrated DMSO solution is used (e.g. 90 percent). Therefore, the practitioner should run a control test with the DMSO solution and no food to determine whether part or all of the immune response reactions observed in other test areas exposed to various DMSO-food mixtures are caused by the DMSO solution. Erythema due to the DMSO solution itself can be "subtracted" from the results observed in other test areas, and the results from the other test areas can be graded accordingly.

For example, if an individual has been found to have a grade 3 immune response to chocolate and the control test for the DMSO solution produces significant erythema corresponding to a grade 1 immune response, the individual can be characterized as having a grade 2 immune response reaction to chocolate.

The DMSO "reaction" can be minimized by using a less concentrated DMSO solution. As mentioned above, an extremely concentrated DMSO solution (90%, for instance) is not essential. Less concentrated DMSO solutions can also be used. Rimso brand solution, a 50% solution of DMSO, is an available agent approved for instillation into the human urinary bladder. It is an example of other utilizable dilutions of DMSO.

It has been determined that certain foods will cause the skin to fluoresce after several days of contact with the skin if the area of the skin exposed to these foods is exposed to ultraviolet light. For instance, when a coffee-DMSO mixture, mixed according to the present invention, is applied in 1-drop quantities to the skin for 2-3 days, the skin will fluoresce after the coffee-DMSO solution is cleaned off the skin upon exposure to an ultraviolet light (approximately 365 n.m. frequency). If, however, the DMSO-coffee mixture has not remained in sufficient contact with the skin for the required period of time, the skin either will not fluoresce or its fluorescence will be significantly reduced. This indicates that the mixture was improperly applied or did not remain in contact with the skin for the required period of time. Of all the foods tested, coffee appears to cause the greatest fluorescence. However, orange, sweet potato, carrot, apple, lettuce, beets and tomatoes have also been found to cause the skin to fluoresce. There are probably other foods not yet tested which also cause the skin to fluoresce. Where a plurality of cells are applied to the skin in a fashion shown in FIG. 1, the "fluorescent" foods should be scattered randomly among the cells 12 so that it is possible to detect whether a portion of the test strip did not remain in contact with the skin for the required time. The reasons for the skin fluorescence in the manner described are not fully understood. A local photosensitivity persists for 10-30 days, and the patient will sunburn in these test sites. The individual must be warned to avoid sunlight to the area.

The foods used in the procedure of the invention can be prepared in two general ways. If the food is eaten after cooking, the food should be cooked and then dried and ground to a powder. It is believed that if the food is eaten after cooking, it should be tested against the skin after cooking as well. Thus, if new chemicals are produced during cooking, they can be tested.

If the food is typically eaten raw, the food should not be cooked. Such foods can simply be dried and ground to a powder. Most fruits and some vegetables can be prepared in this manner for testing. Drying is not essential in either method of preparing the food. Drying simply increases the shelf life of the food and makes it easier to make a DMSO-food mixture.

As mentioned above, when foods are applied to the skin in the manner described above, Types II, III and IV Gell-Coombs reactions can be observed. Heretofore, it was not thought that antibodies associated with Types II and III reactions, namely, IgG and IgM, immune serum globulins were resident under the skin and were sensitized to the foods producing the immune responses. Fluorescent staining, radio labelling, and Hematoxylin and Eosin staining of biopsy materials revealed that IgG, IgM and IgE were present in larger amounts in positive test sites than in untouched sites on the skin. This evidence indicates that Types II and III reactions can be tested intradermally in accordance with the present invention.

It was also surprisingly observed that lymphocytes or T-cells believed to be sensitized to the specific food producing the immune response also became resident under the skin. Therefore, type IV Gell-Coombs immune response could be tested through the skin as well. The DMSO-food mixture method has detected immune response reactions, both to water and fat soluble foods which produce Types II, III and IV Gell-Coombs immune response reactions. This has been found to be particularly useful because only five to ten percent (5-10%) of individuals having immune responses to foods have the Type I reaction. Heretofore, Type I responses were the only reactions which could be satisfactorily tested by means of an intradermal test. As noted above, these tests typically involved either injecting an aqueous solution of the food into the subcutaneous layers or pricking the skin and exposing it to the aqueous mixture. Of course, the present invention requires no injection or prick test. Therefore, it is even simpler than prior intradermal tests.

EXAMPLES

Much practical information concerning the sensitivity and limitations of the DMSO-food mixture method was obtained by selecting patients in whom the ingestant intolerances were already known. Test results using the method of the present invention were compared with results from elimination diet and RAST technique for seventy-four (74) patients. Each patient was subjected to elimination diet testing, RAST and the DMSO-food mixture test method. On the average, for every one hundred (100) positive elimination diet reactions, there were only 5.38 positive RAST reactions. Thus, the RAST test was only 5.38% sensitive. By contrast, the DMSO-food mixture method was 74.41% sensitive. Less sensitivity was expected from the RAST test because it tests only Type I reactions which only ten to fifteen percent (10-15%) of individuals having immune responses to foods experience. However, the 5.38% figure is less than the expected ten to fifteen (10-15%) figure.

The fact that the DMSO-food mixture method produced only 74.41% positive reactions for every 100 positive elimination diet reactions is not entirely unexpected either. The elimination diet technique frequently produces ingestant intolerances not caused by immune responses. For example, ulcers and colitis sometimes result in patients experiencing ingestant intolerances to specific foods and it is obvious that no immune response is involved. Therefore, the 74.41% figure may mean that for every 100 positive elimination diet reactions, 28.59 reactions on the average are non-immune response reactions. It could also mean, however, that the DMSO-food mixture method does not detect all immune response reactions. These non-immune response ingestant intolerance reactions may also partially explain the lower than expected RAST results.

The present method appears to be increasingly sensitive as the age of the patient increases. From the clinical testing, the sensitivity of children aged 12 was only 35.29%. However, this figure dramatically increased to 71.05% for individuals aged 13-27, and increased further still for individuals older than 57 years to 78.31%.

Patients suffering from certain conditions also had statistically significant increased sensitivity to the DMSO-food mixture method. Individuals suffering from joint diseases, including rheumatoid arthritis, musculoskeletal disease, gout, and osteoarthritis were about 86.6% sensitive when compared to the elimination diet test results. Individuals experiencing enuresis were also sensitive to the DMSO-food mixture method. Sensitivity was 75% for these individuals. This corresponds with results from previous studies which are associated in enuresis with type I Gell-Coombs allergies.

Individuals experiencing gastro-intestinal problems, including post-cholecystectomy syndrome, duodenal ulcer, chronic and acute gastritis, colitis, and crohn's disease were 76.9% sensitive to the DMSO-food mixture method using the elimination diet as a comparative standard.

Tests were also performed to determine whether certain foods might be more or less effectively tested by the DMSO-food mixture method. Specially prepared, sterile, freeze-dried, pure food products were individually suspended in 90% DMSO solution (1 gram food to 5 milliliters solution). Each mixture was applied to the upper arm as a patch for three (3) days. Patch test results were recorded by a technician who was unaware of the patients specific ingestant intolerances as determined by elimination diet and/or RAST techniques. The test results were graded as Grades TR, 1, 2, 3, or 4. The following table sets forth data obtained by comparing the results from elimination diet tests with the DMSO carrier method test for given foods. The numerator is the number of positive DMSO carrier method tests that concur with positive elimination diet tests for the given food. The denominator is the total number of positive DMSO carrier method tests checked against elimination diet tests. The fractions are also reported as percentages.

| FOOD | RATIO | PERCENTAGE |
|---|---|---|
| Apple | 8/22 | 36.36 |
| Aspirin | 33/58 | 56.9 |
| Banana | 9/24 | 37.5 |
| Barley | 3/27 | 11.11 |
| Bean | 11/26 | 42.3 |
| Beef | 11/21 | 52.38 |
| Beet | 0/2 | 0. |
| Beet Sugar | 0/1 | 0. |
| Blueberry | 0/2 | 0. |
| Cabbage | 1/5 | 20. |
| Carrot | 0/1 | 0. |
| Chicken | 5/24 | 20.83 |
| Cinnamon | 11/32 | 34.38 |
| Cocoa | 16/28 | 57.14 |
| Coconut | 1/9 | 11.11 |
| Coffee | 14/29 | 48.28 |
| Corn | 16/37 | 43.24 |
| Cucumber | 5/15 | 33.33 |
| Egg | 6/18 | 33.33 |
| Fish | 8/22 | 36.36 |
| Garlic | 3/15 | 20. |
| Grape | 1/2 | 50. |
| Honey | 0/1 | 0. |
| Lactaid | 0/2 | 0. |
| Lamb | 0/15 | 0. |
| Lettuce | 1/3 | 33.33 |
| Oats | 4/23 | 17.39 |
| Onion | 14/32 | 43.75 |
| Orange | 20/33 | 60.60 |
| Pea | 7/24 | 29.17 |
| Peanut | 9/25 | 36. |
| Pepper | 3/17 | 17.64 |
| Pineapple | 0/2 | 0. |
| Pork | 13/25 | 52. |
| Potato (White) | 4/52 | 7.69 |
| Rice | 7/48 | 16.67 |
| Rye | 3/26 | 11.54 |
| Soy | 8/26 | 30.77 |
| Sweet Potato | 1/12 | 8.33 |
| Strawberry | 1/3 | 33.33 |
| Tea | 3/17 | 17.64 |
| Tomato | 16/30 | 53.33 |
| Vivonex | 2/5 | 40. |
| Walnut | 2/6 | 33.33 |
| Wheat | 10/34 | 29.41 |
| Yeast | 1/5 | 20. |

The foods with the lowest numerators are generally classified as hypoallergenic because they typically produce very few elimination diet test reactions. (i.e., three or fewer). From the above table, it can be seen that the foods with numerators 3 or less include apricot, barley, beet, beet sugar, blueberry, cabbage, carrot, coconut, garlic, grape, honey, lamb, lettuce, rye, sweet potato, strawberry, cherry, tea, Vivonex ®, walnut, and yeast. These results agree with results obtained by earlier researchers and with current medical practitioners who consistently choose from among the above foods to construct their patients' basic elimination diets. Foods of intermediate antigenicity as indicated by the DMSO-food mixture method, would be those with numerators between 3 and 8. These foods include chicken, cucumber, egg, oats, pea, potato and rice. This range of numerators was selected because it corresponds with putative knowledge among food allergists that these foods are of intermediate antigenicity. Foods of high allergenicity, i.e., with numerators 8 or greater, are apple, bananas, bean, beef, cinnamon, chocolate, coffee, corn, fish, milk, onion, orange, peanut, pork, soy, tomato, and wheat.

A food with a very low percentage is a food which gives a positive DMSO-food mixture method reaction much more often than it will give a positive elimination diet reaction. This possibly means that certain foods may produce false positive reactions when tested by the present method. These foods include apricot, barley, coconut, rye, sweet potato and white potato. This may also mean that immune responses produced by these foods do not produce discomfort or obvious organ dysfunction symptoms on which positive elimination diet tests are based.

High percentages, on the other hand, (i.e., those greater than about 17%) indicate substances which can be tested using the DMSO-food mixture method with great accuracy. These substances include: orange, chocolate, aspirin, tomato, beef, pork, grape, coffee, milk, onion, corn, bean, banana, fish, apple, peanut, cinnamon, egg, cucumber, soy, wheat, pea, chicken, garlic, tea, pepper, oats and rice. Substances listed in the above table having a percentage greater than 17% not mentioned in the preceding sentence were not statistically significant because the number of individuals tested were small.

Adverse reactions produced by the DMSO-food mixture method have proven to be localized to the area of exposure to the DMSO-food mixture. Routine topical aqueous cortico-steroid spray and cool normal saline soaks control any inflammation in two to three days. In 400 patients tested with the DMSO-food mixture method, none had systemic reactions. Thus, the DMSO-food mixture method is extremely safe.

The data set forth above indicates that the dimethyl sulphoxide food test method in accordance with the present invention is a sensitive and reliable method for assessing immune reactions to foods. The tests detect all four types of Gell-Coombs reactions to food antigens. Based upon the test data, the dimethyl sulphoxide method in accordance with the present invention is probably the most sensitive and most reliable in vivo test for screening food intolerances of immune etiology.

It should be clear from the above tests that the instant method is not restricted to the testing of immune responses to foods, but can be used to detect immune responses to any ingestible substance, including pharmaceuticals, food ingredients such as yeast, or food additives such as Lactaid or Vivonex brand food substitutes.

In view of the foregoing, those of ordinary skill in the art may envision various modifications which would not depart from the inventive concepts disclosed herein. It is intended therefore that the above should be considered only as descriptive of the presently preferred embodiments. The true spirit and scope of the present invention may be determined from the appended claims.

The embodiments of the invention in which an exclusive property or privilege is claimed are defined as follows:

1. A device for the detection of an individual's Gell-Coombs Types I, II, III and IV immune response reactions to test substances, said device comprising:
   a mixture of a test substance and a solution of nontoxic aprotic solvent and water, said solvent having the ability to penetrate skin, and said mixture having a sufficient concentration of said test substance such that an immune response will be produced on the skin if the mixture is applied to the skin of an individual sensitive to said test substance, said solution including at least 20% dimethyl sulfoxide as said solvent; and
   means for holding an amount of said mixture against the skin.

2. The device of claim 1 wherein said test substance is a dried, ingestible substance before being mixed with said solution and said mixture has about one gram of said dried ingestible substance for every five milliliters of said solution.

3. The device of claim 2 wherein said dried, ingestible substance is a cooked substance.

4. The device of claim 2 wherein said ingestible substance is a pulverized substance before being mixed with said solution.

5. The device of claim 2 wherein said means for holding holds at least 0.05 milliliters of said mixture.

6. The device of claim 1 wherein said means for holding said mixture against the skin comprises:
   a plurality of cells, each cell having an open side for contact with the skin, and each of said cells holding an amount of said mixture with each amount containing a different test substance, said amount being sufficient to produce an immune response in an individual sensitive to said test substance;
   absorbent means within each cell for absorbing said mixture and holding said mixture inside the cell and against the skin;
   adhesive means for adhesively securing said cells against the skin; and
   means carried by each of said cells for preventing the aprotic solvent within said cells from dissolving said adhesive means and carrying said adhesive means through the skin.

7. The device of claim 6 wherein said means for preventing comprises an O-ring placed around the circumference of the open side of said cell and wrapping means for preventing said O-ring from being dissolved by said aprotic solvent and being carried through the skin.

8. The device of claim 6 wherein said absorbent means comprises cotton.

9. The device of claim 6 wherein said absorbent means comprises methyl cellulose.

10. The device of claim 6 wherein at least one of said cells contains a mixture of dimethyl sulfoxide and a food which causes the skin to fluoresce after about 3 days of contact with the skin.

11. A mixture to be applied to the skin for determining whether an individual has a Type I, II, III or IV Gell-Coombs immune response to a particular edible substance, said mixture, comprising:

a solution of a non-toxic aprotic solvent and water, said solvent having the ability to penetrate the skin; and an edible substance mixed with said solution and being of sufficient quantity in said solution that a Gell-Coombs Type I, II, III or IV immune response reaction can be produced on the skin of an individual sensitized to said substance when a small amount of said mixture is applied to the skin.

12. The mixture of claim 11 wherein said aprotic solvent is dimethyl sulfoxide, and said solution consists of about 20% aprotic solvent and the balance consisting essentially of water.

13. The mixture of claim 12 wherein for every one gram of said edible substance, there are five milliliters of said solution.

14. The mixture of claim 11 wherein for every one gram of said edible substance, there are five milliliters of said solution.

15. In a test strip having a plurality of cells containing ingestants for application to the skin to determine an individual's immune response to one of said ingestants, the improvement comprising:

at least one of said cells containing a food which causes the skin to fluoresce when exposed to ultraviolet light, said fluoresence providing an indication of how long the test strip has been in contact with the skin.

* * * * *